US006832877B2

(12) United States Patent
Hamada

(10) Patent No.: US 6,832,877 B2
(45) Date of Patent: Dec. 21, 2004

(54) DENTAL MEASURING AND MACHINING SYSTEM

(75) Inventor: Hiroaki Hamada, Tokyo (JP)

(73) Assignee: Kabushiki Kaisya Advance, Tokyo (JP)

( * ) Notice: Subject to any disclaimer, the term of this patent is extended or adjusted under 35 U.S.C. 154(b) by 0 days.

(21) Appl. No.: 10/296,841

(22) PCT Filed: May 29, 2001

(86) PCT No.: PCT/JP01/04509

§ 371 (c)(1),
(2), (4) Date: Nov. 26, 2002

(87) PCT Pub. No.: WO01/91664

PCT Pub. Date: Dec. 6, 2001

(65) Prior Publication Data

US 2003/0123943 A1 Jul. 3, 2003

(30) Foreign Application Priority Data

May 29, 2000 (JP) ...................................... 2000-158374

(51) Int. Cl.[7] ............................................... B23C 1/16
(52) U.S. Cl. ......................... 409/96; 409/235; 409/201; 33/560; 33/503; 33/505; 700/161; 700/163; 74/490.01
(58) Field of Search ...................... 104/96, 94; 700/163, 700/161; 409/235, 201; 74/490.01; 33/503, 505, 560; 433/219, 213, 223, 51

(56) References Cited

U.S. PATENT DOCUMENTS

| | | | | | |
|---|---|---|---|---|---|
| 3,869,799 | A | * | 3/1975 | Neuer et al. ................... | 33/561 |
| 5,257,203 | A | * | 10/1993 | Riley et al. .................. | 700/163 |
| 5,440,496 | A | * | 8/1995 | Andersson et al. .......... | 700/163 |
| 5,449,256 | A | * | 9/1995 | Sundman .................... | 409/134 |
| 5,452,219 | A | * | 9/1995 | Dehoff et al. ................ | 700/163 |
| 5,539,649 | A | * | 7/1996 | Walsh et al. ................. | 700/163 |
| 5,715,729 | A | * | 2/1998 | Toyama et al. ........... | 74/490.03 |
| 5,906,461 | A | * | 5/1999 | Lunz et al. .................. | 409/201 |
| 6,212,442 | B1 | * | 4/2001 | Andersson et al. .......... | 700/194 |
| 6,568,936 | B2 | * | 5/2003 | MacDougald et al. ....... | 433/223 |

FOREIGN PATENT DOCUMENTS

| | | | |
|---|---|---|---|
| DE | 019720049 A1 | * | 11/1998 |
| JP | 05-138560 | | 6/1993 |
| JP | 8-281581 | | 10/1996 |
| JP | 9-10232 A | * | 1/1997 |
| JP | 9-10241 | | 1/1997 |
| JP | 10-47941 | | 2/1998 |
| JP | 10-176902 A | * | 6/1998 |
| JP | 10-192305 | | 7/1998 |
| WO | WO 91/02496 | | 3/1991 |
| WO | WO 98/30176 A1 | * | 7/1998 |

OTHER PUBLICATIONS

International Search Report of PCT/JP01/04509, dated Jul. 24, 2001.

(List continued on next page.)

*Primary Examiner*—Erica E Cadugan
(74) *Attorney, Agent, or Firm*—Christie, Parker and Hale, LLP

(57) ABSTRACT

A dental measuring and machining system includes a measuring and machining unit for preparing measurement data by measuring a prosthesis model based on a predetermined algorithm and for producing a prosthesis by machining a prosthesis block based on the above measurement data, and an operating unit for operating the measuring and machining unit from the outside. A user is able to produce a dental prosthesis by operating the measuring and machining unit under the control of a computer. The measuring and machining unit is connected to the external operating unit by communication, and the measuring and machining unit can be operated from the outside.

4 Claims, 10 Drawing Sheets

OTHER PUBLICATIONS

International Preliminary Examination Report of PCT/JP01/04509, dated Mar. 27, 2002.

Patent Abstract of Japan, Publication No. 08281581 A, Published on Oct. 29, 1996, in the name of Nippon Steel Corp.

Patent Abstract of Japan, Publication No. 09010241 A, Published on Jan. 14, 1997, in the name of Matsushita Electric Ind Co Ltd.

Patent Abstract of Japan, Publication No. 10047941 A, Published on Feb. 20, 1998, in the name of Mitsutoyo Corp.

Patent Abstract of Japan, Publication No. 10192305 A, Published on Jul. 28, 1998, in the name of Advance Co Ltd.

*Journal of the Japan Robot Society*, Oct. 1992, pp. 63–69, vol. 10, No. 6.

\* cited by examiner

DENTAL MEASURING AND MACHINING SYSTEM

CROSS-REFERENCE TO RELATED APPLICATION

This application is a National Phase Patent Application of International Application Number PCT/JP01/04509, filed on May 29, 2001, which claims priority of Japanese Patent Application Number 2000-158374, filed May 29, 2000.

TECHNICAL FIELD

The present invention relates to a dental measuring and machining system.

BACKGROUND ART

For producing a dental prosthesis such as an implant, inlay, bridge or crown, an apparatus, by which a suitable dental prosthesis is formed by preparing three-dimensional measurement data by measuring the shape of a model sampled from a defective part of the teeth or jaw and so forth, and machining a block of a material optimum for a prosthesis based on the measurement data, is proposed. This type of apparatus uses a computer for controlling the function for numerically encoding and computing data, and the function for driving a cutting drill based on this computed data to machine the block by grinding or cutting. Generalization and increased efficiency of the computer is realized under a practical level by the combination of general-purpose OS and CAD/CAM software, so that the apparatus can be operated easily even if a user does not have detailed and specialized knowledge in the fields of dentistry or machinery but can understand the manner of use to a certain extent. For example, an example of such an apparatus is Dental Measuring and Machining Apparatus "CADIM" (registered trademark) (made by Advance Corporation).

In this manner, even in the case of an apparatus by which a dental prosthesis can be produced with specialized dental knowledge as long as the manner of use can be understood to a certain extent, if the user does not fully understand the use of a computer, or if the user understands the use of a computer, it is required to deal with erroneous operations or rare cases, and the situation is unchanged so that the user must learn to the extent necessary to overcome such problems.

In addition, since there are individual differences in the shapes of defective parts of teeth or jaw shape and so forth, the prostheses are always forced to custom-made production, and automated mass production is unexpected, forcing them to be handled on a case-by-case basis.

Moreover, even if the computer has a high degree of universality and its operation is not that much different from the operation of routinely used personal computers, since a beginner still has to learn to operate the computer, and that operation has the special nature of measuring and machining dental prostheses, there are still cases in which specialized operations for adjusting software or additional information is required depending on the addition, revision or alteration of its functions.

Thus, although the support of a person having a certain degree of specialized knowledge is required for use, since there are many cases in which simply sending a document or a floppy disk to the user and having the user perform operation are not adequate, ultimately resulting in the need to dispatch a trainer to the user's location, as the area covered expands, it becomes necessary to contend with a large burden in terms of both cost and labor in order to accommodate this situation.

Moreover, although contact measurement using a probe or non-contact measurement using an optical technique such as laser light are employed as methods for measuring the surface shape of a model obtained from the oral cavity of a patient in order to obtain an accurate prosthesis, the contact type is preferable in terms of seeking accuracy.

However, in the case of the contact type, since it is necessary to manipulate the probe so that is makes contact with the entire surface of the model, in addition to requiring considerable time, it is also necessary to rotate and move the model for that purpose.

In addition, since a conventional probe is composed in the shape of a single rod positioned horizontally on the so-called Z axis, and comes out at locations where measurement is difficult, it becomes necessary to change the position of the model more carefully.

This type of tedious manipulation requires a considerable amount of learning by the dentist and so forth that uses it. In addition, since the driving parts for moving the probe, the grinding tool and the cutting tool become large, this type of measuring and machining equipment takes up space, and there is a case in which its installation is difficult for a small-scale dental practitioner, etc.

Moreover, although computerized measuring and machining is useful in terms of simplifying the conventional, tedious machining process and reducing cost, on the other hand, the noise produced during machining by the machine tool portion for dental cutting results in a difficult situation for performing in parallel with dental treatment.

In addition, even if operation of the machinery for measuring and machining is premised on the use of a general-purpose computer, since it is necessary to learn how to operate the computer, the machinery cannot be used immediately.

In addition, although varying somewhat depending on the measurement technique, the amount of time spent on a series of measuring and machining takes about a half day even if the user is familiar with the operation.

In addition, since there are some prostheses that are made of pure titanium and so forth that cannot be machined by a general-purpose machine tool, there are limitations on the types of prostheses that can be machined.

Therefore, by separating the measuring section and machining section, and having the dentist, dental technician or other user retain only the measuring section, while installing the machining section at an external, specialized facility, together with reducing the burden on the user, various other advantages are obtained, including being able to produce all types of prostheses, and enabling the user to be freed from the noise of the machine tools.

However, in the case of transmitting data from the measuring machinery to the machining machinery, since dental prostheses inherently having defective parts of irregular shapes or have large shapes such as in the case of full implants, there are many cases in which a large amount of data is required. Consequently, a considerable amount of time ends up being required for transmitting all measurement data, thereby resulting in the problem high so-called secondary cost in the form of public telephone line connection cost, equipment investment cost and so forth.

SUMMARY OF THE INVENTION

In consideration of the above, the present invention enables sharing the information within a dental measuring and machining apparatus or bidirectionally transmittable conditions through a communication medium, and realizes the production of a prosthesis, that allows direct and practical distribution of a software for improving a measuring and machining function (version-up), maintenance of software, etc., consultation for persons performing similar measuring and machining as well as the provision, manipulation and handling of various other information considered to be beneficial, real-time customer management, and the receiving and placing of orders for blocks for prosthesis formation, other instruments and machinery, outside measuring or outside machining, while also enabling transmission and receiving operations on data for reproducing measuring and machining operations on the user side at a support side, to thereby fully demonstrate the inherent functions of the apparatus even if the user is a beginner.

An algorithm in the present invention refers to a program or data, which includes software, data and so forth relating to CAD/CAM software, NC software, a measuring section and machining section, including the general program for driving the equipment of the measuring section and machining section, or data obtained as a result of that, and data that contains the parameters for arbitrarily running the program, although not limited to those.

The outside in the present invention refers to a region other than a machinery and instrument that execute measuring and machining, and covers various locations from a broad range extending to both at home and abroad to a narrow range such as within the same room.

In another aspect of the present invention, the dental measuring and machining apparatus is provided with a probe having contacts that extends in the directions of a cross for contact measurement of the surface of a model for producing a prosthesis, surface shape acquisition means for obtaining the shape of the surface of the above model based on contact by the above probe, and machining means that performs machining processing by a cutting and grinding tool on a model for machining a prosthesis based on the data of the above surface shape acquisition means. As a result of having this constitution, the surface shape of the model can be adequately measured while minimizing movement of the model, thereby making it possible to reduce the burden on the user.

Moreover, the present invention realizes stable measurement of the surface shape of a model while holding a probe in a stable manner on which the weight burden is increased in a complex manner by using a parallel link structure for the drive unit that drives the probe, and while performing highly accurate operation extremely easily and enabling the overall size to be reduced.

Moreover, the present invention enables highly accurate models to be formed at high speed and without taking up space while also allowing the obtaining of highly accurate prostheses by employing a constitution in which the compact measuring section and the machining section are separated, data of the measuring section is transmitted to the outside, and the prosthesis is formed based on this transmitted data, and a constitution that combines a cross probe with a parallel link drive unit that drives it.

The cross probe in the present invention refers to a constitution in which, for example, contacts or so-called styluses are extended in the positive and negative directions of the X axis and Y axis centering about the Z axis within three-dimensional coordinates.

Each of the contacts, in addition to presenting a rod shape extending linearly, may also be formed into a curves shape or composed in the shape of an acute angle.

Although the example of the contacts shows a vibrating type provided with a vibrator composed of a piezoelectric material that vibrates a vibrator at the site where the contact is connected, and a detector also composed of a piezoelectric material that detects changes in the resulting vibrations when the contact has contacted a model, there are also cases in which other techniques are used.

Preferable examples of this cross-type probe can be referred to in the technologies described in Japanese Unexamined Patent Publication No. 10-47941 and Japanese Unexamined Patent Publication No. 10-176902.

The parallel link structure in the present invention is preferably used by, for example, a so-called robot manipulator as described in the Journal of the Japan Robot Society, Vol. 10 (1992) pp. 757–763.

A parallel link has a composition in which, for example, both ends of two sets each of a total of six serial link drivers, which extend and contract by the driving of a linear motor, are connected in parallel at three locations on a drive side support plate and support base (Stewart platform type), or a composition of a three-shaft or six-shaft type, and has a composition in which a potentiometer, which obtains angle information and other positional information of a so-called joint section composed on the link end, is respectively connected to each drive side support plate on the driving end side.

A parallel link allows high-speed movement simply by driving the motor of each drive member to expand and contract, and has an extremely simple composition. In addition, since a parallel link drives as a result of being supplemented by a plurality of driving parts, it is suitable for driving heavy objects, and in addition to being able to be used preferably in the case of using a cross-type probe having a complex structure and being somewhat heavy as in the present invention, since control of the parallel link can be performed simply by controlling the motor, it is capable of performing extremely high-speed movement of the probe.

Although preferable examples of the composition of a parallel link can be referred to in the technologies described in Japanese Unexamined Patent Publication No. 5-138560 and Japanese Unexamined Patent Publication No. 8-281581, the composition is not limited to these, but rather is only required to have a composition in which driving members are linked in so-called parallel. Furthermore, since a three-shaft type of parallel link is composed by only using three serial links, it is preferable in terms of costs.

In still another aspect of the present invention, it has been made possible to produce a dental prosthesis that is capable of withstanding prosthetics by extracting data of its characteristic site and then performing supplementary work. In this manner, since only data of the characteristic site is required to be sent, shortening of transmission time can be realized, thereby realizing a system that does not place a burden on users.

The characteristic site in the present invention, in the case of a crown for example, indicates three pieces of data consisting of data on the occlusal surface of the model for producing the prosthesis, data on the site from the occlusal surface to the maximum lateral projection, and data on the contact line between the abutment and crown (margin line), or data on sections of the prosthesis having sudden projections, or data indicating the oral cavity environment such as height, width and so forth during occlusion in the case of partial or full dentures.

More specifically, since the neck is obtained numerically from the sum of the margin and projection, the characteristic site consists of margin line data and projection line data, and this portion is transmitted.

Since the cement space and coping shape are obtained numerically from the abutment surface, the portion of the abutment surface data is transmitted as the characteristic site.

Furthermore, since the abutment surface data is also obtained from the apex and bottom line data, only this portion may also be transmitted as characteristic section data. Since intraconal crown shape data and other double crown data and so forth are also obtained numerically from margin line data, conus angle data and conus height data, margin line data, conus angle data and conus height data may also be transmitted as characteristic sections.

Supplementary work refers to supplementing missing shape data obtained with characteristic site data and parameters with straight lines, planes, curved lines and curved planes. Bezier, spline and other curve processing means are used as specific supplementation techniques.

There are cases in which prostheses produced on the basis of this degree of transmission data are superior to prostheses produced by transmitting all data in terms of compatibility, stress diffusion and durability.

BEST MODE FOR CARRYING OUT THE INVENTION

Figure 1:
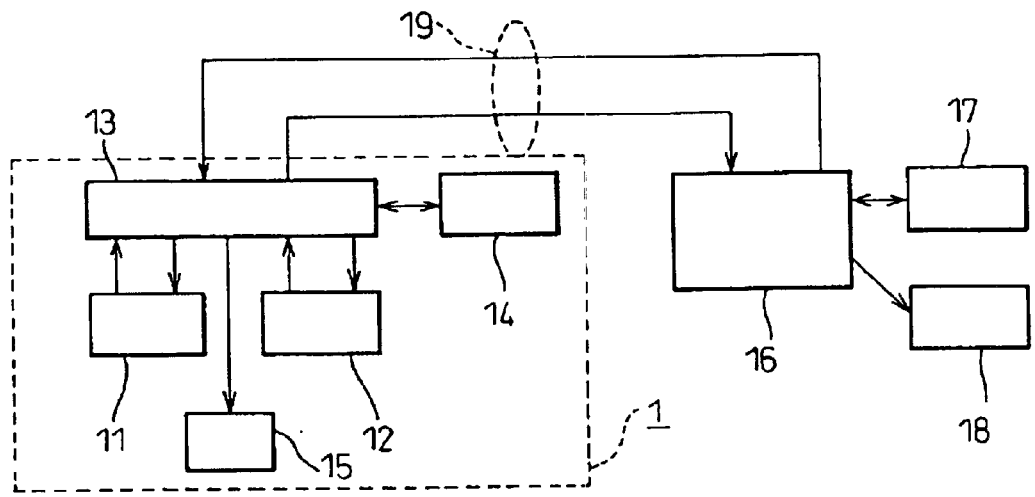
FIG. 1 is a view showing an embodiment of a measuring and machining system according to the present invention.

In FIG. 1, a measuring section 11 is provided with a probe to measure the shape of a model as an object for measurement such as a prosthesis, to prepare data from the measurement, and to output the data. A machining section 12 is provided with a machining device such as a drill, a rotary cutter and so on to machine a work such as a block as an object of prosthetics, by grinding or cutting, based on the input data.

Control section 13 is primarily composed by a computer, and has peripheral terminals for interconnecting internal and external devices such as a monitor 15, a memory 14, a modem, a network card and so on various other internal and external devices, to interconnect and control these devices. Moreover, the control section 13 controls the driving of the probe of measuring section 11, and controls the function for converting data obtained by the measuring section 11 into machining data and the driving of the machining device in the machining section. These elements compose a measuring and machining terminal 1.

Figure 2:
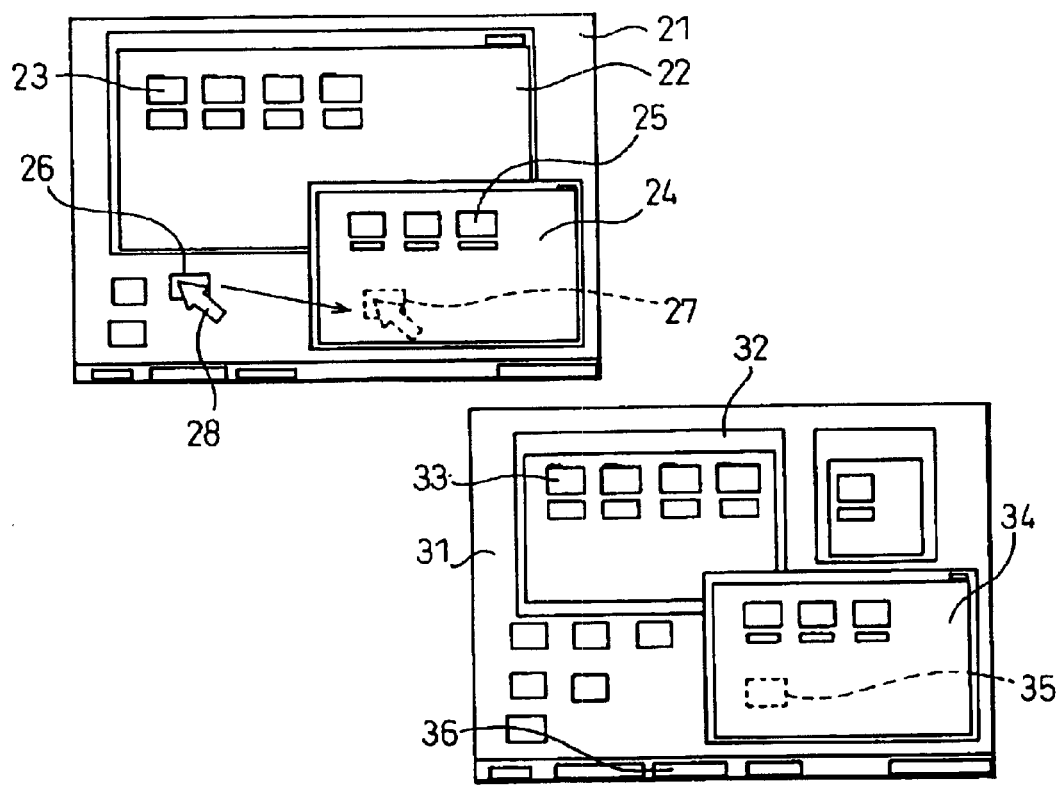
FIG. 2 is a view showing the displays of the server and the measuring and machining terminal of FIG. 1.

Reference numeral 16 indicates a server which is primarily composed by a computer and controls the input and output of a memory 17 and the output to a monitor 18. Server 16 is also provided with various other interfaces such as a modem and a network card. Data of measuring and machining terminal 15 for every user are recorded in the memory 17 of the server 16, and the data are preferably depicted in the form of icons as shown in FIG. 2. Reference numeral 19 indicates a telecommunication line, examples of which are a wired line such as the Internet or telephone line, and a wireless line such as a portable telephone (although not limited to these). Server 16 and the measuring and machining terminal 1 have equipment that enables connection with communication line 19.

Furthermore, when using public communication such as the Internet, it is preferable that at least transmitted and received data be processed, by coding, for example, so that they cannot be viewed by a third person, and processing is preferably performed on the terminal 1 so that data other than the required data are not received so that the data and the program in the terminal 1 are not destroyed. Server 16 may also be provided with a measuring section and a machining section in the same manner as the terminal 1.

The following provides an explanation of FIG. 2. Reference numeral 21 indicates the display of the monitor 18 of the server 16. Reference numeral 22 indicates a window for the measuring and machining terminal 1, while reference numeral 23 indicates an icon group indicating more detailed functions. For example, they are measurement data, measurement execution data, machining progress data and machining execution data, and, by double-clicking on any of these, for example, a window 22 opens and the measuring and machining terminal 1 can be executed according to the purpose in the window.

Reference numeral 24 indicates the state in which a portion of the window is opened. Reference numeral 25 indicates a file contained therein which contains previously executed old version data and other data. Distinction between new and old data is selected according to, for example, file names or update times.

Reference numeral 26 indicates a newly created execution file, reference numeral 27 indicates the state after a new execution file has been moved by a drag-and-drop procedure by a cursor 28.

Reference numeral 31 indicates a display of the monitor 15 in the measuring and machining terminal 1, while reference numeral 32 indicates a shared file with the server 16. Icon group 33 corresponding to the previously mentioned icon group 23 of the server 16 is formed therein. Reference numeral 34 indicates a window corresponding to the window 24 of the server, and an icon 35 is formed corresponding to the icon 27 dropped on the server side 16. Reference numeral 36 indicates a display area that is also called a task bar, and the input of a new file can be notified by flashing this area on and off, for example, The data of the individual measuring and machining terminal contain the kind of the machine, the production information, the maintenance record, the data transmission and receipt record, the software version information and so forth, and the program data for measuring and machining that is stored in the individual measuring and machining device is also stored.

Moreover, the server 16 is able to exchange data synchronous to each measuring and machining terminal 1.

This information is layered in the form of icons, and the window is in a synchronous state with control unit 13 within each measuring and machining terminal, namely, in the state in which the data are stored directly in the memory 14 of control unit 13, for example, by dragging and dropping data to a window like that shown in FIG. 2 displayed on the monitor 18 of the server 16. This function can be realized easily by the web sharing of one of the functions (using browser software), the remote access sharing, or the network sharing such as by using an FTP (file transfer protocol) function and so forth, if a computer such as a GUI controlled by the current window operation is used for the control unit 13 and the server 16.

Moreover, in addition to sharing of the data, the present invention also has a function for monitoring the actual operation of the measuring and machining terminal 1. Namely, server 16 is able to acquire output from the measuring section 11 and the machining section 12 during driving thereof, on nearly a real-time basis or at least at a speed corresponding to the situation, enabling the server 16 to directly control the driving of the measuring section 11 and the machining section 12.

At that time, the status may be displayed on a specific window on the display of the server 16 as shown in FIG. 2, and in this case, the operation of each measuring and machining terminal 1 is monitored by this server 16, and can be remote controlled by dragging and dropping of files and so forth.

On the other hand, the exchange with the server in each measuring and machining terminal 1 is carried out in a minimally layered data area. Namely, this area is, limited to one window of the monitor 15, for example, and the transfer of data to there is such that the data move to the area of the corresponding terminal of the server 16, and may have an execution area that operates automatically, if data is transmitted from server 16 and in the case of new data that has not been used, according to identification by the type of file, namely the file name. Thus, the server manages the terminals in the state in which the user is not particularly required to view that area, resulting in a preferable state particularly for beginners.

A more concrete case is now described.

When the user is a beginner and is not familiar with the manner of use, the user calls up the server 16 directly. In this case, both may have a videophone function, and in that case, questions and responses can be made on a real-time basis and may be terminated in the case when the user understands. This may also be in the form of transmission and reception by written documents using electronic mail.

In the case if this is inadequate, a display for operation may be shown on the monitor 15 of measuring and machining terminal 1. In other words, the display shows where the user should actually click on the screen or what the next step is. In this case as well, it is preferably that this be carried out via a certain shared data area, and execution is selectively carried out according to the file name or window area.

Server 16 first moves the file showing the first step (e.g., image file (and containing audio data depending on the case)) to the user's own monitor 18. At that point, it is temporarily stored in the control section 13 and the memory 14 of the measuring and machining terminal 1 together with the execution status. Furthermore, in this case, the user may at least perform an operation so as to allow file transmission in order to form the execution state. Thus, the server 16 allows execution by each measuring and machining terminal. Namely, execution may be made to be allowed only in the case windows and icons have been made active (by single-clicking, for example).

This type of operating method guidance is particularly preferable for users having no prior experience of use, when at least the use of help software contained in advance by the terminal is not adequate. Furthermore, since costs become a problem in the case of using a network on a real-time basis in this manner, all required files may be initially dropped to the window in response to a request from the user. In this case, the file names may be ordered and then executed in order at the request of the user or automatically.

Next, in the case of providing an upgraded program from the server 16 to the control section 13 of each measuring and machining terminal 1, updating may be executed simply by dragging and dropping (26 to 27) that file to a predetermined file name or window using a mouse (such as 110 in FIG. 3) corresponding to the cursor 28 so that the program is updated. Furthermore, since the size of such a program itself becomes large, file transmission may be carried out either by compressing or replacing only those locations that change.

In addition, in the case a new file is transmitted by the server 16, the display area 36 on the window, the icon or the task bar may be made to flash so as to notify the user. In addition, a simple message may be displayed on the image by specifying such as by single-clicking or using a shortcut key in response to that flashing.

In the case when the user is unable to measure well or machine well, the user informs this situation to the server 16. In this case, the details are sent to the window in the sharing state. Server 16 views the content and in the case when the reason is unknown, it peruses measurement record data by selecting from the window and analyzes that data, and also the server 16 directly drives the measurement section 11 of measuring and machining terminal 1. The manner of this driving may be performed by, for example, dropping the file to a specific window. Although measurement data and progress data are formed by this driving, this data is also automatically placed in the shared area, after which the server 16 confirms the data by arbitrarily viewing the file.

In the case when the data can be used directly as machining data, the server 16 drops the file to the area for its execution. As a result of this dropping, the measuring and machining terminal 1 is informed that data has been transmitted and after the message is transmitted, the preparation such as the attaching the block, and the machining are executed. The data on the execution of the machining is preserved in the shared file, and the server 16 may then examine the cause of the problem by viewing that file.

In addition, in the case when the cause of the trouble is on the machining side, operation may be performed by dropping the measurement data obtained in advance or the measurement data sent from the measuring and machining terminal 1 into that window, and the server 16 may be allowed to gather the progress and result data from the window and to examine the data.

Furthermore, it is possible to reduce the labor of the user, and to reliably form the prostheses, by operating the measuring and machining terminal 1 by remote control in this manner by the server 16. Maintenance is also placed in the shared area, and the server 16 may be made to be able to refer to this shared area as necessary.

Furthermore, in the case when the server 16 and the individual measuring and machining terminals 1 share a file, cost of a prescribed amount may be charged per unit time at least for shared execution and operation in the case when there is a request from a user, and account transfer and so forth may be used to make payment.

Moreover, the present invention is made such that a user possesses a measuring section 11 only, and measurement data is created by compressing and organizing measurement data to an area suitable for communication, after which a machining facility that also serves as the server 16 is accessed from a user site to transmit this measurement data. Server 16 then performs a series of machining, including adjustment and finishing, based on said measurement data, and then sends this by mail and so forth. Although this type of mode is realized with the constitution shown in FIG. 4, since a user does not have to have a machining section in this method, reduced size, lower cost, reduced learning of CAD and other special techniques, and lower noise level are achieved, thereby reducing the burden on the user, which is more preferable for installation at dental clinics and so forth operated by individuals.

Figure 3:
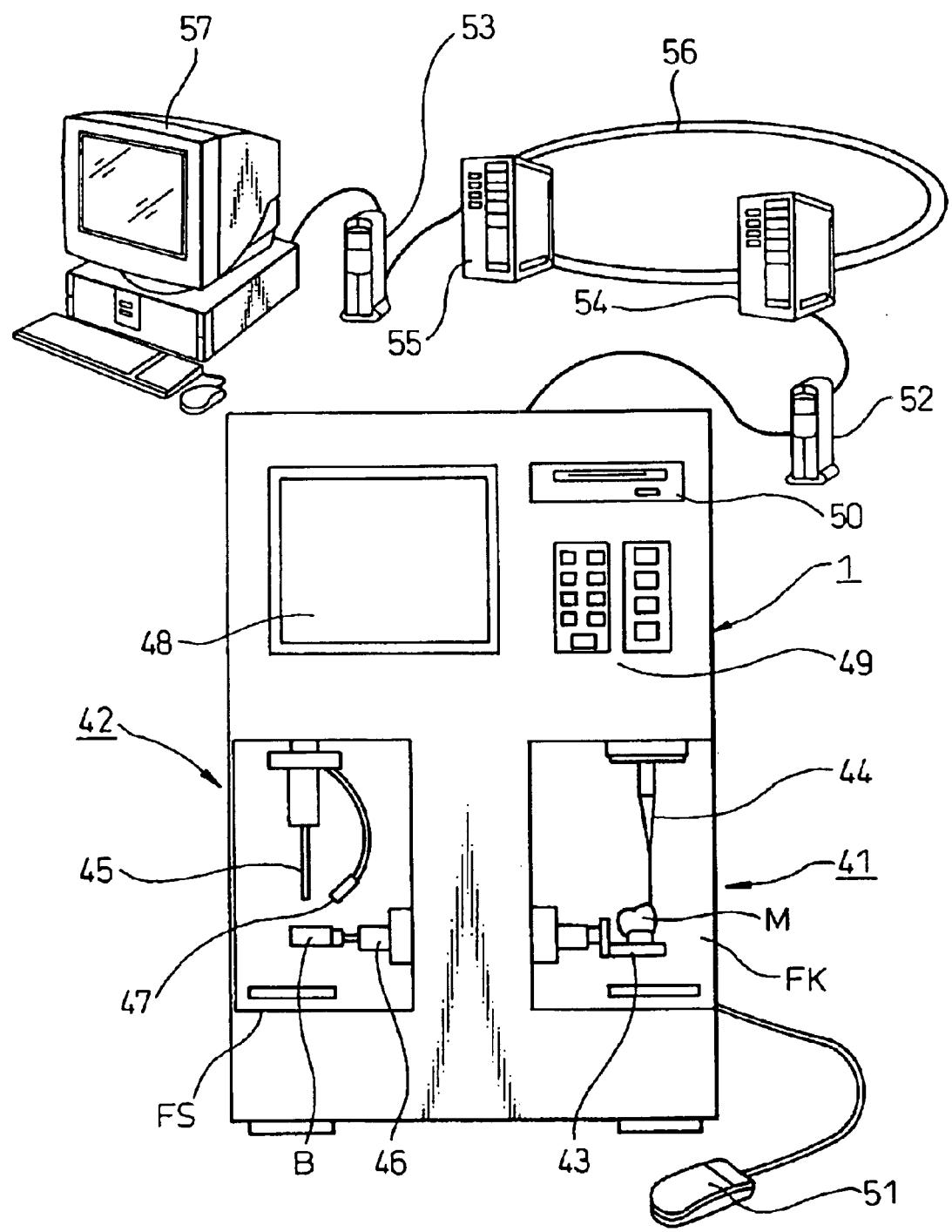
FIG. 3 is a view showing a more detailed example of the measuring and machining system according to the present invention.

Next, explanation is provided of a more specific embodiment for carrying out the present invention as shown in FIG. 3. FIG. 3 shows a more specific example of the measuring and machining terminal 1 and so forth shown in FIG. 1. Measuring and machining unit 1 is a main body of a dental measuring and cutting apparatus providing with a section for measuring the shape of an object, and a cutting section for managing the shape data obtained by said measuring, and cutting a block composed of a prosthetic material based on said data. In the measuring section 41, a model M is placed on a measuring stage 43 that manually or automatically rotates, and preferably slides, a measuring probe 44 is in contact with the model M, and the surface shape of the model M is measured based on the amount of displacement of the measuring probe 44.

Machining section 42 is provided with a vertically and horizontally slidable rotary drill 45 and has a support stage 46, which is capable of rotating or sliding either manually or automatically depending on the case, and which supports block B comprised of a material that can be used as a bioprosthesis made of ceramics such as hydroxyapatite or metal such as titanium. Moreover, a nozzle 47, which outputs water for washing away from the block B cuttings produced during grinding and cutting when the rotary drill 45 contacts block B, is arranged so as to be driven by being coupled to the rotary drill 45.

Transparent covers FK and FS that open vertically or horizontally are formed on both the measuring section 41 and the cutting section 42 for preventing scattering of cuttings and protecting the measuring section, etc.

Monitor 48 is a section mainly for display of measurement and cutting status as well as operation. Panel switches 49 are mainly for adjusting measurement and cutting operations by pressing and so forth. Panel switches 49 are provided with a function for connecting them to the server regardless of the operation of the internal computer, and preferably have a function that is activated when they are pressed to notify the server by a simple message of an error in said terminal or an emergency situation such as in the case of desiring to produce a prosthesis on an emergency basis even though the user is unfamiliar with the usage method.

Reference numeral 50 indicates a drive section for reading or writing a storage medium depending on the case. Examples of the storage medium are a floppy disk, MO, CD-ROM and so on, and the drive section is suitably selected according to the storage medium. Mouse 51 indicates and activates an icon on the screen of monitor 48 with a pointed that is linked to the movement of a mouse, or is used to form an image on the monitor screen with a pointer. Depending on the case, this may be able to be operated more easily than operating panel switches 49.

Although at least a general-purpose computer is contained in the main part of the measuring and machining terminal 1, which in addition to performing composite and arithmetic processing of measurement data, can be made to perform the measuring operation through the use of known CAD technology, since the present invention mainly indicates a pre-measurement processing process, a program based on that process is executed, and preferably stored either temporarily or permanently.

More preferably, another computer is contained that controls the driving of the rotary drill for cutting. Furthermore, according to the constitution of said apparatus, modeling can also be performed simultaneously to and in conjunction with measuring and cutting, and by installing a video or still image monitor in the space of the measuring section 41 and the machining section 42, the range of remote control may be able to be further expanded.

Reference numerals 52 and 53 are modems or network cards which are data transfer and conversion devices for sending and receiving data via an external or internal telecommunications line. Reference numerals 54 and 55 indicate connection mediation means in the manner of a provider in the case when the telecommunications line is the Internet, for example, which also serve as temporary storage means and so forth for web sites, electronic mail, etc., and refer sections that have storage means that can be used by each user. Reference numeral 56 indicates a telecommunications line, such as a public line, local line or wireless line. Reference numeral 57 indicates a server that is a section for performing transmitting data to a user, receiving data and performing remote control and so forth.

The following provides an example of operation. The server 57 is connected to telecommunications line 56 via the modem 53 and the connection mediation means 55, and at this time, there are also cases in which it is preferable to open a web site that can be accessed freely by a third party at connection mediation means 55. The telecommunications line and additionally measuring and machining terminal 1 connect with connection mediation means 54 via the modem 52, and a storage unit that temporarily accumulates so-called mail and other data is accessed at connection mediation means 54. This storage unit and so forth are not particularly necessary, and instead, corresponding terminals employing a dialup type of RAS (remote access system) and so forth, in which modems are connected with a telephone line, may also be connected.

Furthermore, since there are cases in which telephone charges and other costs are incurred, it is more economical and preferable to use data temporarily stored in the storage unit of connection mediation means 54, rather than a real-time connection.

Display 21 of FIG. 2 corresponds to the monitor display of the server 57, while the display 31 corresponds to the monitor 48 of the terminal 1. To begin with, the server 57 opens the icon of measuring and machining terminal 1 of FIG. 2 to form the window 22. Moreover, the icon that is the objective of transmission is opened, to form window 24, and the icon 26 is moved thereto by dragging and dropping with the cursor 28 to form the icon 27.

As a result of this action, data is stored in the memory of the measuring and machining terminal 1 of the connection mediation means 54 via the modem 52, the connection mediation means 55 and the telecommunications line 56. Measuring and machining terminal 1 incorporates this data with a procedure for downloading mail. The incorporated data is automatically or manually moved to a shared icon and dropped to the window 34 corresponding to the window 24 of the server 16.

As a result of single-clicking on this window while in this state, the target contents are executed automatically. The results are converted to a data file and sent to the server in a state like that of mail transmission. This type of operation is suitable since it reduces costs as a result of shortening connection time and so forth.

In addition, in the case when the measuring and machining terminal 1 accesses a web site opened at the connection mediation means 55 by the server 57, accesses data from this web site and then acquires and sends back the required data, data may be sent to the server 57 using the procedure for mail transmission.

Moreover, as a result of machining a remote access network using a telecommunication line, file sharing may be performed to realize real-time operation as in the explanation of the operation of FIG. 1.

Figure 4:
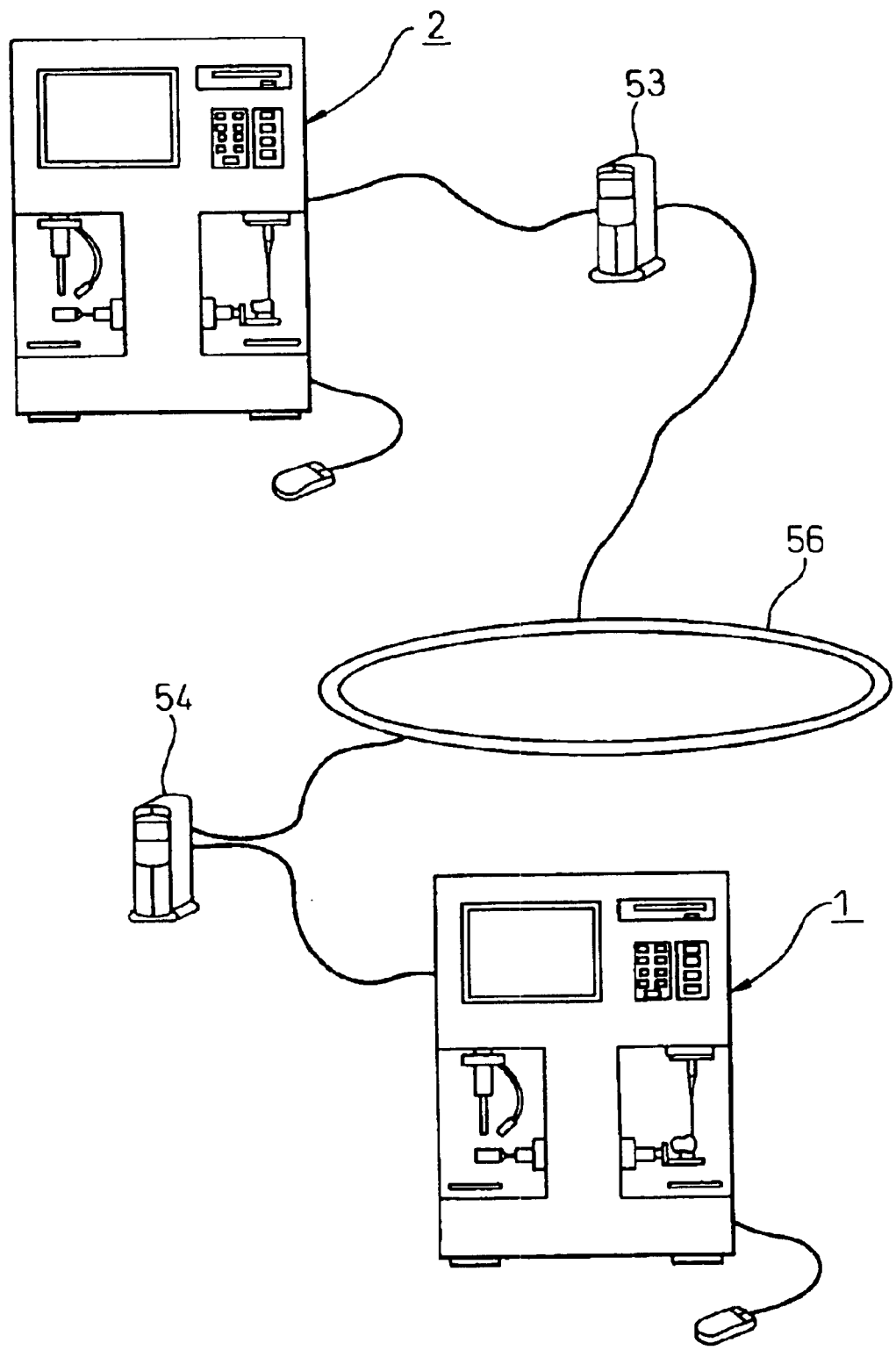
FIG. 4 is a view showing a variation of the measuring and machining system according to the present invention.

Moreover, the measuring and machining terminal 1 may also be made to function as a server as in FIG. 4. In this case, this can be accommodated by modifying to the extent simply increasing the capacity of the storage means. Reference numeral 2 indicates a server, while reference numeral 1 indicates a measuring and machining terminal. Other constituent features are assigned the same reference numerals as FIG. 3, and the explanation is omitted. Furthermore, although the connection mediation means is omitted in FIG. 4, it may be connected as necessary.

According to the present embodiment, the server 2 is able to perform the same functions by being linked with the measuring and machining terminal 1, and can provide support with respect to finding the cause of a problem or when a prosthesis cannot be formed on the terminal side. Namely, as a result of data generated based on the movement of the probe operated at the terminal being transmitted to the server 2, together with operating the probe in the same manner, data information in the case of having been obtained while the probe contacts model surface data can be transmitted to the server 2, the presence of a problem can be determined or maintenance can be performed, and in addition to driving the machining section to have it perform a similar machining operation based on that data, the machining operation data on the terminal side can be transmitted to the server 2, and the server 2 can be made to perform the machining operation based on that data, thereby making it possible to confirm problems in the machining section and perform maintenance.

In addition, the server 2 can also be made to directly drive the measuring section and the machining section of the terminal 1. For example, a user presses a button used for direct connection of the panel switch 49 shown in FIG. 3. When the button is pressed, simple data information is transmitted to the server 57, or a display or warning sound and so forth is emitted based on the fact that the button is pressed. Depending on the case, although contact may be made by telephone without pressing the button, since operation of the device is required in any case, there is a case in which contact is made automatically mediated by the device.

A user at least places the measurement model M on the measuring stage 43, and places the block B on the support stage 46. Server 57 then directly controls the driving of the measuring section 41 and the machining section 42 based on this data. Namely, a command for operating the probe is output to the control unit, and as a result, the resulting data is temporarily stored in the terminal's memory. Subsequently, a machining data is formed by instructing the creation of the machining data to the terminal's control unit.

In this case, the resulting data does not necessarily have to be received directly by the server, but may be temporarily stored by the terminal so that only its operation is controlled, or if the data can be transmitted electronically, that data is copied. After production of the machining data is completed, the server 57 outputs the machining data to the measuring section so as to drive measuring section 41.

Furthermore, in the case of the server driving the measuring and machining terminal directly in this manner, although online operation over the Internet is preferable, on the other hand, in order to shorten connection time, the server may initially send the execution data of a series of measuring operations to a terminal, and after terminating the connection between the server and the terminal, and after the terminal is notified the server that the data is executed, the measurement data is received from the terminal, a series of data for executing measurement is sent, the connection between the server and the terminal is terminated, and following its completion, in order to receive machining-related data after machining, the connection between the server and the terminal may be restored in the manner of intermittent connection and usage. In this case, a display exchange between the terminal and the server may be carried out by one or more windows on the server side.

As is described in detail above, the present invention enables the production highly accurate dental prostheses regardless of user status.

Another embodiment of the present invention is explained in detail with reference to FIG. 5.

Figure 5:
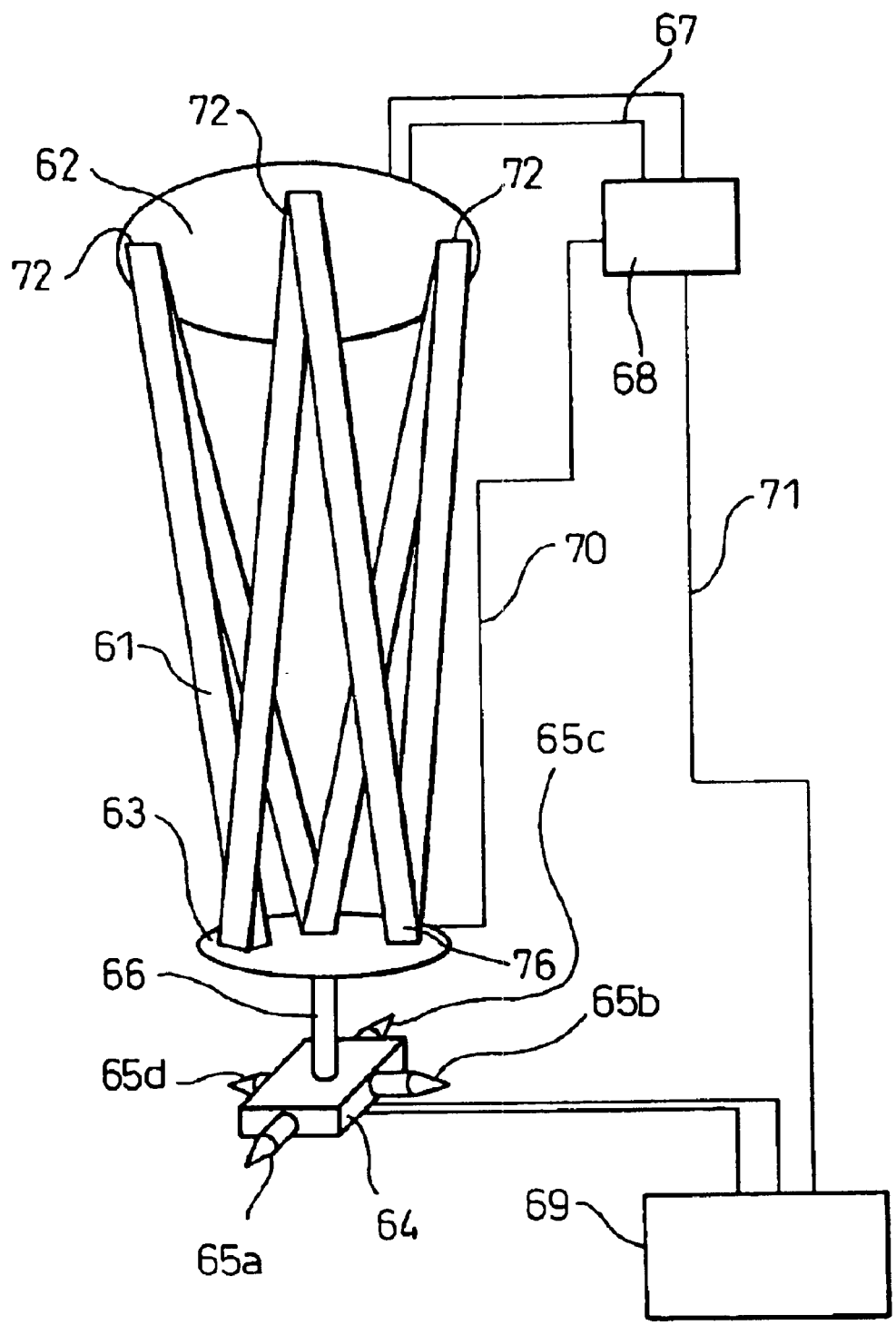
FIG. 5 is a view showing another embodiment of the present invention including a parallel link and a cross probe.

In FIG. 5, reference numeral 61 is a drive unit that has a so-called serial link structure. Six drive units 61 are connected in a zigzag pattern between base plate 62 and terminal support body 63, machining a Stewart platform type. This should be understood to only represent one example, and a type may also be employed in which three shafts or six shafts are connected straightly. The specific structure of each drive unit 61 is shown in FIG. 6, and the detailed explanation thereof is made later.

Base plate 62 is a portion for connecting the measurement device main unit and the drive units 61 and for connecting it with one ends of respective drive units 61. Terminal support body 63 connects it with the other ends of respective drive units 61 and is connected to a support shaft 66 of the probe.

Detection unit 64 is a portion that generates contact and non-contact information of contacts 65a through 65d. Although not shown in the drawing, vibration elements, vibration displacement detection elements and so forth are mounted on the detection unit 64 so as to make contact with each contact. Contacts 65a through 65d may also be referred to as styluses. The end needle-shaped portion is the contact, and each contact is connected to the detection unit 64, and make a contact connection with vibration elements and vibration displacement elements. Vibration elements and vibration displacement elements may be arranged so that their lateral surfaces make contact with needle-shaped styluses 65a through 65d. Support shaft 66 connects the terminal support body 63 and the detection unit 64.

Figure 6:
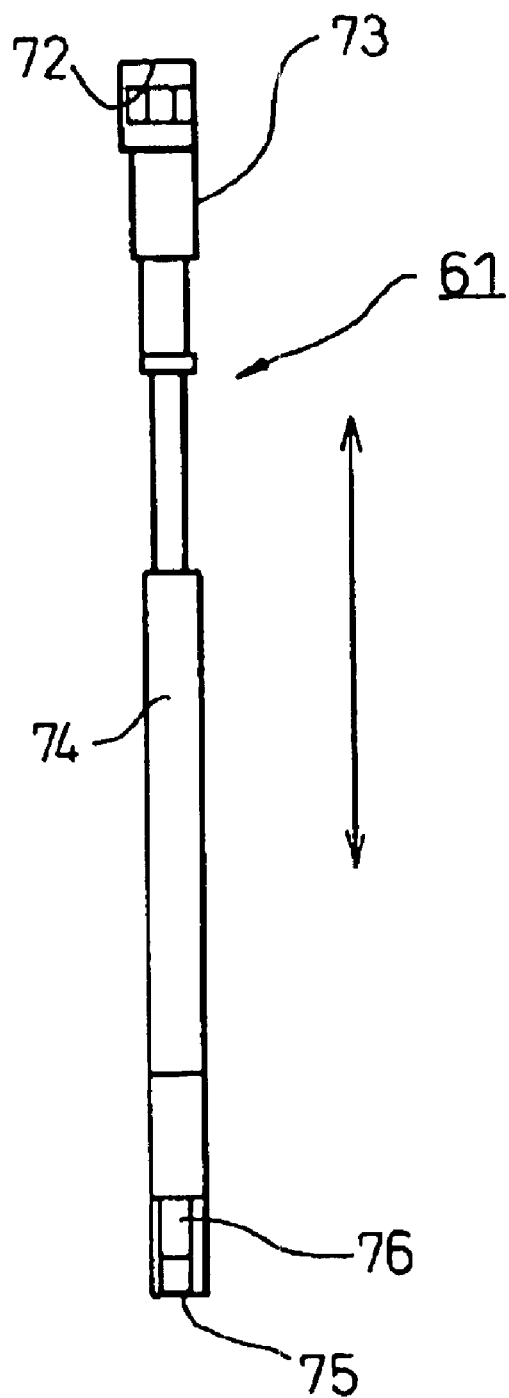
FIG. 6 is a view showing a drive unit of FIG. 5.

Reference numeral 67 indicates an electrical connection member for outputting a drive signal to a motor 73 shown in FIG. 6 of the drive units 61. Reference numeral 68 indicates a drive signal output unit that is for outputting drive signals to the motor 73.

Reference numeral 69 indicates a control means that receives signals output from the detection unit 64, calculates the positional information of the model from the information obtained by each contact 65a through 65d making contact with the model, accumulates that information and outputs that information to a machining means.

Control means 69 is also for generating the next movement position of the probe and outputting that position to the drive signal output unit 68. Reference numeral 70 indicates a transmission unit for outputting angle information that indicates the manner of bending of the joint of each link end output by a potentiometer 76 to drive signal output unit 68. Reference numeral 71 indicates a transmission unit for transmitting the signal from control means 69 to drive signal output unit 68.

A specific example of the structure of each drive unit 61 is shown in FIG. 6. Reference numeral 72 indicates a connection end that has a joint capable of rotating 360 degrees. Reference numeral 73 indicates a motor that is formed by that having a composition in which position-controllable linear driving is performed based on an electrical signal, or is formed by a linear motor. Reference numeral 74 is a sliding member that is coupled to the motor 73 and slides in the lengthwise direction. Reference numeral 75 indicates the other end that has a joint capable of rotating. Each other end 75 is connected to the terminal support body 63. Reference numeral 76 is a potentiometer that outputs angle information of the joint of the other end 75 in the form of an electrical signal.

Figure 7:
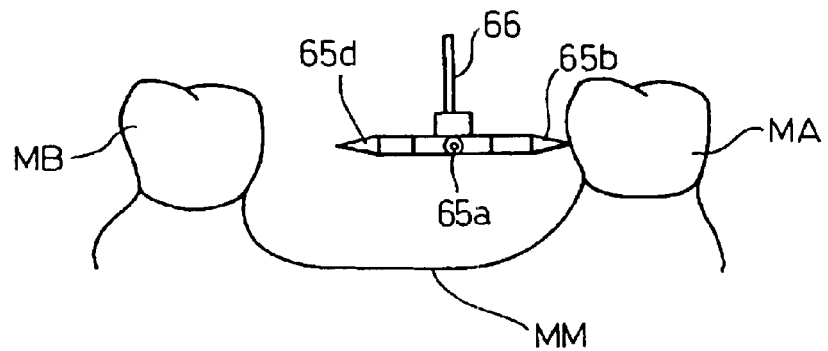
FIG. 7 is a view explaining the operation of the apparatus of FIGS. 5 and 6.

The following provides an explanation of an example of the operation of FIGS. 5 and 6 with reference to FIG. 7. A bridge type model MM produced in advance is placed on the measuring stage, and the drive signal output unit 68 outputs a signal for driving the motor 73 of the drive unit 61 until the contact 65b makes contact with the surface of a model tooth MA as shown in FIG. 7 in the state in which a rough movement pattern of the positional information of the contacts is recognized. Each drive unit 61 is extended and contracted by the driving of the motor 73 to move contact 65b.

When the contact 65b contacts the surface of the model tooth MA, the detection means 64 outputs a signal to the effect that the surface is detected to the control means 69. At that time, the control means 69 outputs a signal to stop further movement in that direction to drive the control output unit 68. Drive signal output unit 68 outputs a signal to that effect so as to stop operation of the motor 73 of each drive unit 61, after which the direction of the next movement is determined based on joint angle information and so forth sent from the potentiometer 76, while the amount of motor driving is determined from the positional information of each contact 65a through 65d of the probe, after which this is output to the motor 73 of each drive unit 61.

As a result of repeating in the above manner, the other contacts are contacted and make contact with the surface of model tooth MA to generate its surface shape data.

Next, the probe moves in the direction of the model tooth MB shown in FIG. 7 in the manner of the operation described above, contact is made with the model tooth surface MB primarily by the contact 65d, the drive unit 61 is partially extended and contracted at the comparatively flat portion of the model upper surface, an angle is imparted to terminal support body 63 and the detection unit 64, each contact makes contact, and the surface data is transmitted to the control means 69. Other surface data is then obtained by repeating this operation.

In this manner, by contacting a probe having a plurality of contacts with a model surface, its surface data can be obtained in a shorter period of time without moving the model.

Minimizing the movement of the model not only eliminates bothersome work on the part of the user, but also simplifies the constitution of the section on which the model is placed.

Figure 8:
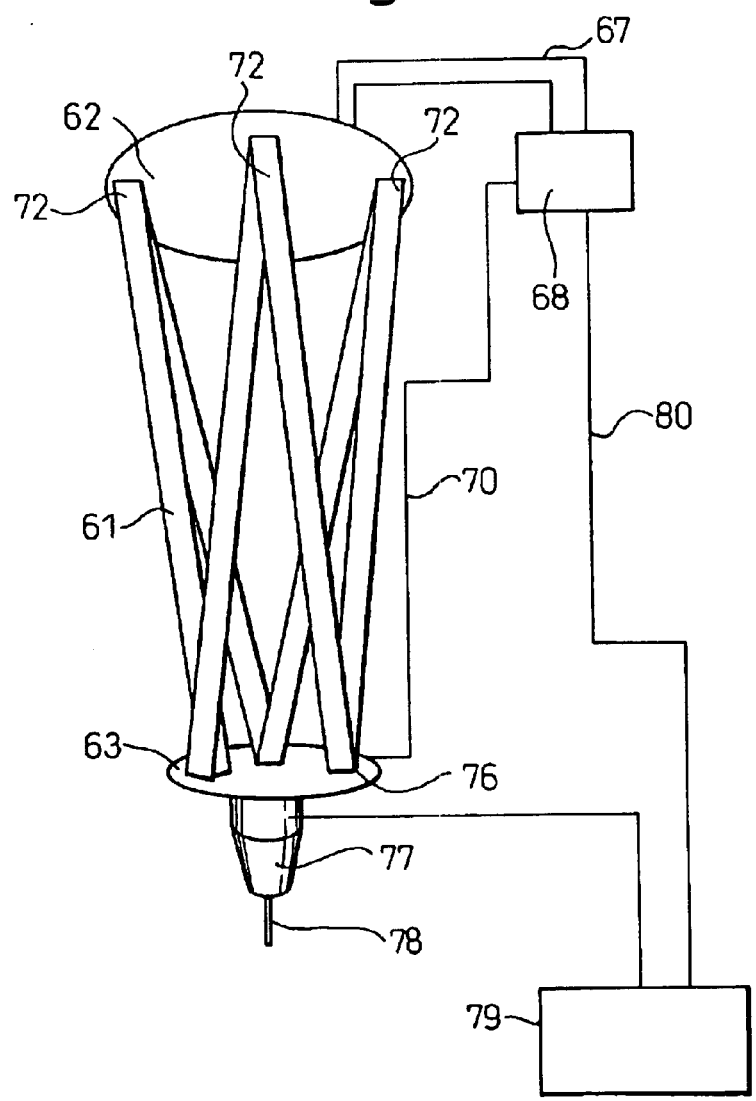
FIG. 8 is a view showing an arrangement similar to that of FIG. 5 including a parallel link and drill.

Next, explanation is provided of an example of the constitution of the machining section as shown in FIG. 8. FIG. 8 shows a constitution in which a machining drill is attached to the drive body having the parallel link structure shown in FIG. 5. Those sections that are the same as the constitution shown in FIGS. 5 and 6 are indicated with the same reference numerals, and their explanation is omitted. Reference numeral 77 indicates a motor for rotating the grinding drill 78. Reference numeral 79 indicates a control means, which in addition to controlling the driving of the motor 77, transmits data to drive signal output means 68 that controls the movement of the drive units 61 based on received measurement data. Reference numeral 80 is a connector for transmitting a signal between the control means 79 and the drive signal output means 68.

With respect to the operation resulting from the use of the above constitution, although essentially the same as that shown in FIG. 5, as a result of using a machining means having drivers that use a similar parallel link in order to withstand high speeds since measurement takes place at high speeds in the case of using a parallel link in measurement, there are cases in which it is possible to suppress the burden on arithmetic processing of arithmetic control.

Figure 9:
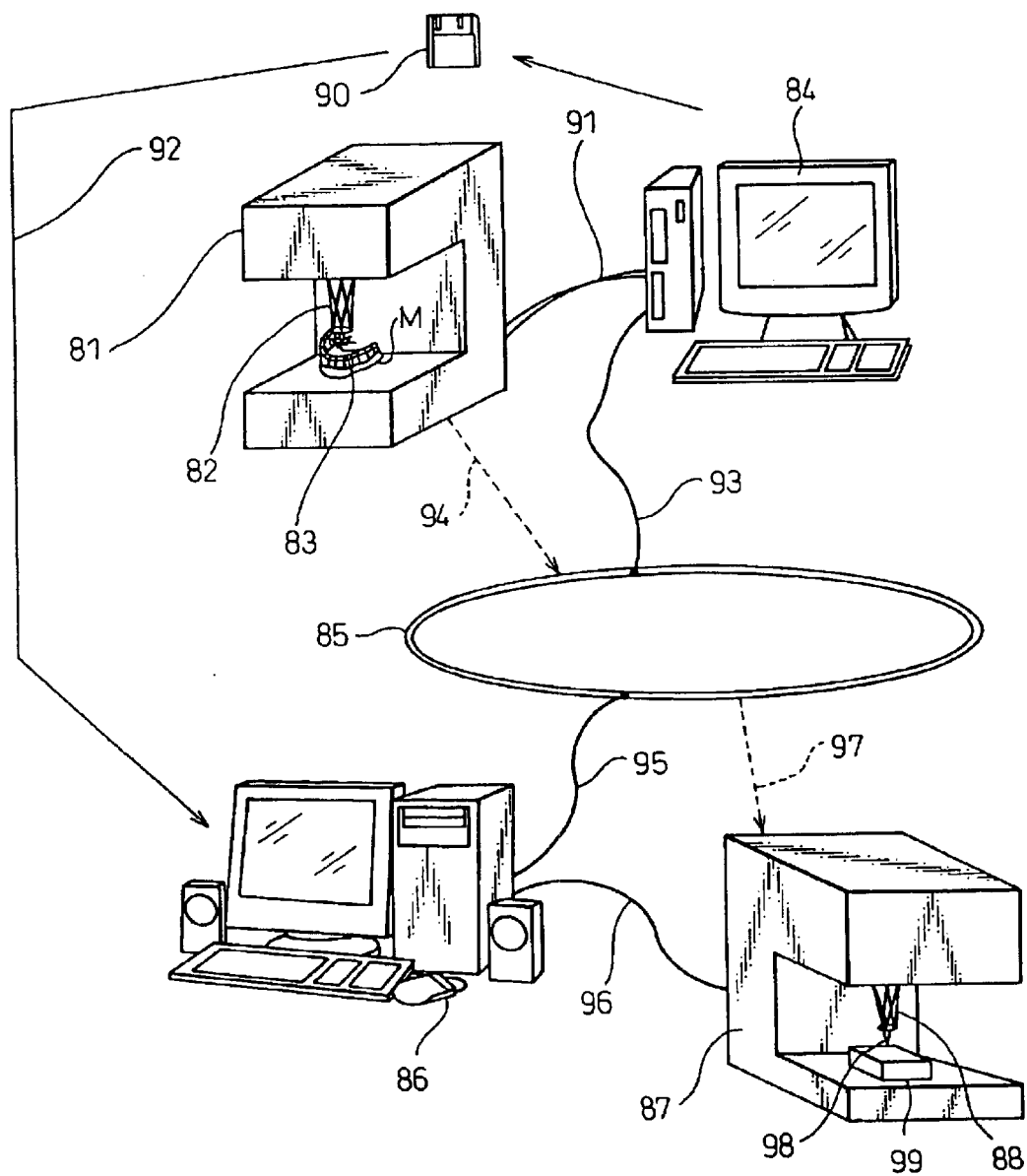
FIG. 9 is a view showing the overall arrangement of the apparatus of FIGS. 5 through 8.

The following provides a detailed explanation of the overall constitution of the system shown in FIGS. 5 through 8, with reference to FIG. 9. Reference numeral 81 indicates a measurement device main unit, while reference numeral 82 indicates a parallel link driver like that shown in FIG. 5. Reference numeral 83 indicates a cross probe, while reference numeral 84 indicates a measurement processing unit for control of the operation of the measurement device main unit and for input and processing of the form of surface data obtained as a result of the cross probe making contact with a model.

Reference numeral 85 indicates a network that may be a general-purpose network or dedicated network. Examples of general-purpose networks include the Internet and personal computer communications, and, although not shown in the drawing, a modem, a connection service or a service provider and so forth is located at an intermediate point on the network. Examples of a dedicated network include an LAN, an intranet, or a local connection using a dial-up format. Furthermore, this section is not limited to a wired form such as a public line, but rather also includes wireless forms such as infrared rays and radio waves. In this case, a means is incorporated for transferring data to a wireless medium such as a modulation means or demodulation means.

Reference numeral 86 indicates a machining processing unit for receiving model surface data and converting this received data to machining data and so forth to control machine tools used for machining. These processing means for measurement and machining can both be adequately replaced with computers for personal use.

Reference numeral 87 indicates a machining device. Machining device 87 is provided with a machining tool 98 used for the purpose of cutting and grinding, and a drive unit 88 that drives it. Since the purpose of the driving unit 88 is to enable an accurate prosthesis to be cut and ground from a block, although there are no particular restrictions on its constitution, the machining device is preferably driven by a parallel link as shown in FIG. 6, and since the machining tool can be driven faster and more accurately by synchronizing its driving information, a parallel link structure is preferably employed.

Reference numeral 99 indicates a block to be machined. Although the block to be machined may be any type of block provided it can be used as a prosthesis, highly pure titanium is preferable because of its superior biomiscibility along with its light weight, durability and aesthetic properties. Moreover, hard ceramics are preferably used for members for which machining is difficult with simple machining devices.

Reference numeral 90 indicates a recording medium, and should be a portable recording medium such as a floppy disk, MO, CD-R or Memory Stick. Reference numeral 91 indicates a connector that is a cable based on the USB, SCSI, RS232C or LAN transmission format. Preferably, the connector consists of a connection relationship and cable that is universally connected to a general-purpose computer. Reference numeral 92 indicates a transport means in which transport is carried out by a means such as mail, home delivery or hand-carrying. Reference numeral 93 indicates a network connection, and indicates a connection state in which data is transferred over a line via a modem. A public line or private line and so forth are located at an intermediate point in this connection. Reference numerals 94 and 97 indicate connectors in the case of the measuring device and machining device being directly connected with the network 85 with going through each processor 84 and 86. In this case, either the measuring device or the machining device is provided with a modulation-demodulation means such as a modem as a transmission and reception means. Reference numeral 95 indicates a connector for connecting with a network in the same manner as reference numeral 93.

The following provides an explanation of operation.

A model is obtained in advance from an oral cavity. Model M is obtained by filling a hard member into the defective portion of a tooth and then removed after hardening. The surface of the model M is measured using the cross probe. The measured data is transmitted to measurement processing unit 84 via the connector 91. Measurement processing unit 84 reconstructs the measurement data internally and makes arbitrary adjustments in the measurement data, compresses the data and performs other processing followed by transmitting it to machining processing unit 86.

In this case, it may be transmitted to the machining device using the transport means 92 after recording on the recording medium 90, or may be transmitted via the network 85.

In the case of transmitting via the network 85, it is transmitted via the connector 93 to a partner provider through a provider if the network is, for example, the Internet. At the partner provider, the data is stored temporarily until it is requested by the machining processing unit.

In the case of processing by electronic mail, the data is temporarily recorded in an e-mail storage unit, after which the machining processing unit 86 reads this temporarily recorded via the connector 95. Alternatively, the data may be read directly in the case of a direct connection state in the manner of a computer chat forum or Internet telephone. In addition, if the measurement processing unit 84 and the machining processing unit 86 share data on the network, data may be transmitted such that the machining processing unit 86 copies the measurement data within the measurement processing unit 84, or measurement processing unit 84 moves the measurement data to a folder inside the machining processing unit 86 that shares data. After the machining processing unit 86 receives data via the connector 95, it creates machining data based on that data as well as other material request data from the user, and connects this to the machining device 87 via the connector 96.

Machining device 87 moves the drive unit 88 and the cutting tool 98 based on this data to cut and grind the block 99. After the block 99 is machined into the shape of a prosthesis, it is sent to the dentist or dental technician on the measuring side by mail, hand-carrying or home delivery. Furthermore, in addition to the case of the cutting device being on the outside in this manner, both may be possessed and used by connecting directly. In this case, both processes may be handled by a single computer instead of having two processing units, or these processing units may be internalized and integrated into a single constitution.

For example, FIG. 9 shows the case of the combination of the measuring device main unit 81→the connector 91→the measurement processing unit 84→the connector 93→the network 85→the connector 97→the machining device 87. In this case, the system is composed such that the measurement processing unit 84 performs the remote control of the operation of machining device 87 in the manner of, for example, a network printer, allowing the user to perform to carry out machining arbitrarily. In FIG. 9, for example, the case of the combination of the measuring device main unit 81→the connector 94→the network 85→the connector 95→the machining processing unit 86→the machining device 87 is shown. In this case, a constitution is employed wherein the machining processing unit 86 performs the remote control of the operation of the measuring device main unit 81 in the manner of, for example, a network printer, and the user simply places the model in the system, while a person with specialized knowledge performs the measuring and the machining by remote control.

As described in detail above, the present invention has the effect of enabling the production of a prosthesis both at high speed and high accuracy while minimizing the burden on a user.

FIGS. 10 through 13 are views showing still another embodiment of the present invention.

Although each of these figures explains the shape of the model obtained from the defective portion of a tooth or the shape of a prosthesis which is produced by the present invention, on the other hand, they are also virtually displayed on a display by making three-dimensional measurements of the surface and reproducing numerically obtained data with a personal computer, and therefore, they are numbered based on the depiction of each constitution in the form of data.

Figure 10:
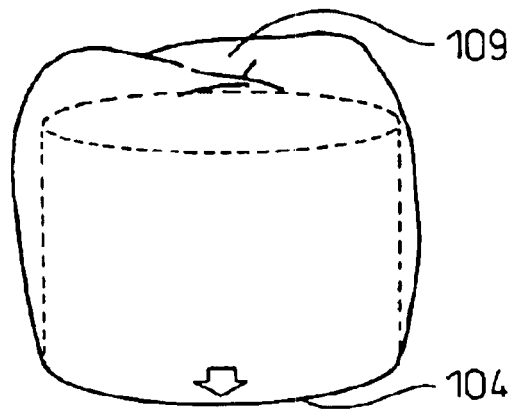
FIG. 10 is an exploded view showing another embodiment of the present invention in the case of producing a conus type of prosthesis.
Figure 10:
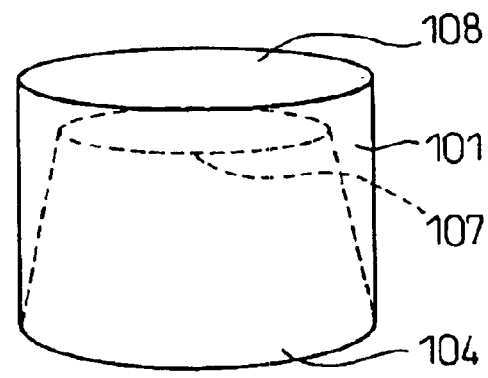
Figure 10:
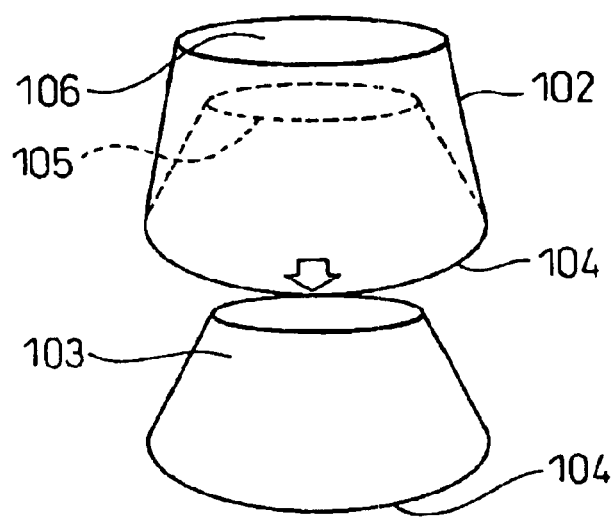
Figure 11:
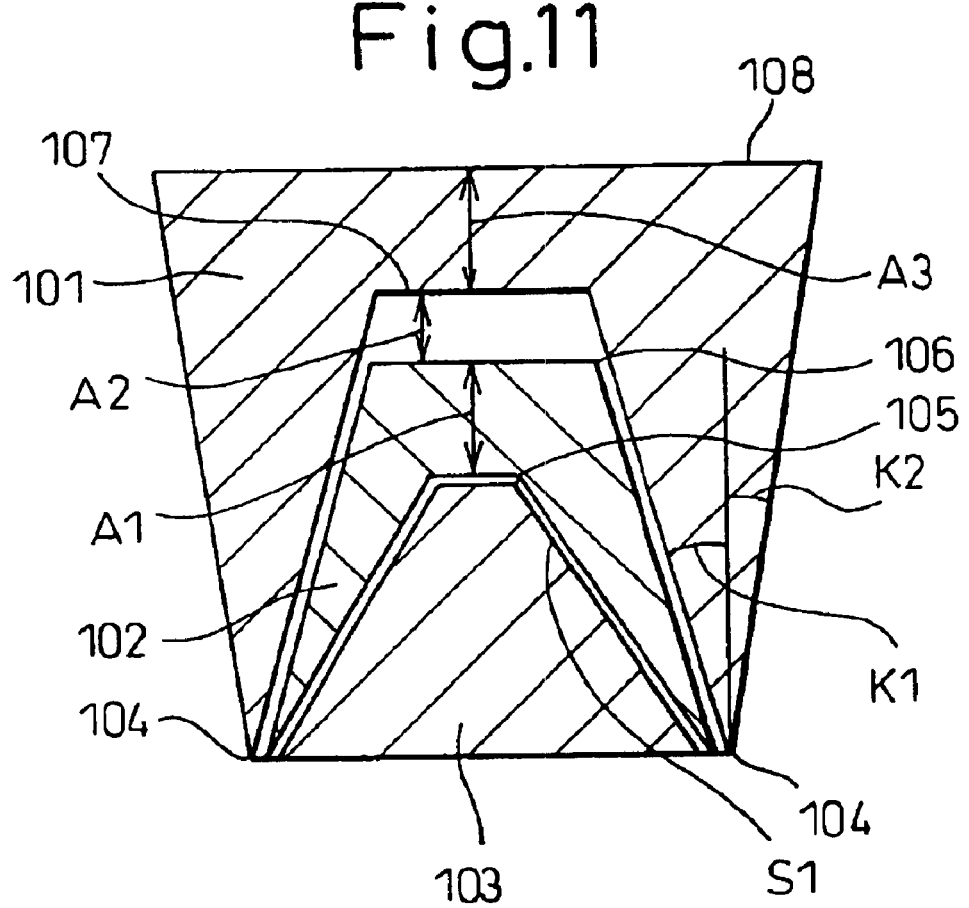
FIG. 11 is a cross-sectional view with the elements of FIG. 10 being combined.

FIGS. 10 and 11 are explanatory views in the case the prosthesis produced is of the conus type.

Conus Type Data Production Procedure

A conus (conus cronen telescope, conus telescope) is a conical double crown proposed by K. H. Körber and is composed of an inner crown 101 and its conforming outer crown 102.

The axial surface of the inner crown 102 is subjected to milling by attaching a conus bar or a conometer to a parallelometer to impart a suitable conus angle. Typically a six degree conus angle is imparted, but a retention force can be changed by suitable adjustment. Retention force is obtained by the wedge effect due to contact between the inner and outer crowns and the metal elasticity (elastic deformation) of the outer crown. This is mainly applied as a retaining device for partial dentures.

The conus angle refers to the angle of half of the cone angle formed by extending the taper of the axial surface of the inner crown of a conus cronen telescope. The inventor, K. H. Körber, reported that the most suitable retention force is demonstrated when a conus angle of six degrees is used.

FIGS. 10 and 11 show the shape of a model obtained from the defective portion of a tooth, and the shape of the prosthesis obtained by replicating the shape of that model.

Model Formation

A model is formed of the site of an abutment 103 by filling plaster, resin or metal and so forth into the impression surface (negative mold) in which an impression is taken directly from the defective portion within the oral cavity of the patient. Moreover, a denture model 109 is formed that is attached to the surface of the abutment. Outer crown 101 is produced so as to achieve an accurate positional relationship with the abutment 103, and the portion equal to or lower than the maximum projection is not required to be produced.

Denture model 109 is ultimately completed in the form of a denture (conus telescope denture) by soldering the corresponding outer crowns and partial plate, etc. followed by laser welding or packing with porcelain. A conus telescope denture refers to a partial denture in which a conus telescope is used as the retaining device.

Inner crown 102 is attached to abutment 103, and outer crown 101 is connected to the denture. Reference numeral 105 indicates the inner surface of inner crown 102, while reference numeral 106 indicates the outer surface of inner crown 102. Reference numeral 107 indicates the inner surface of outer crown 101, while reference numeral 108 indicates the outer surface of outer crown 101.

Measurement of Model Surface

Measurement of the model surface is carried out by a three-dimensional measuring instrument provided with a non-contact method using a laser or a contact method using a probe and so forth. Margin line 104 is made to be able to be discriminated by measuring the upper surface of the abutment or trimming the lower portion of the margin. The margin line refers to the contact line where the prosthesis and body tissue make contact in the outside direction, and this portion is required to be measured accurately since conformation of this portion prevents secondary carious.

This trimming is produced so as to be compatible with the manner of measurement of the three-dimensional measuring instrument. For example, since the margin line is indicated with a line as previously described, the model is formed so that there are projections at this portion to facilitate contact measurement, or a colored line is made so as to easily reflect or absorb laser light.

During measurement of the denture upper surface, the upper surface of the denture is measured with the denture conforming to the abutment 103.

Setting Parameters from Measurement Data

Margin line 104 is detected from the measurement data of the abutment 103. The maximum projection line is detected from the surface measurement data of denture model data 19. The conus angle (degrees) (indicated with K1 in FIG. 11), the thickness of the upper portion of the inner crown (mm) (indicated with A1 in FIG. 11), the conus gap (mm) (indicated with A2 in FIG 11) and so forth are then determined. Conus angle K1 and the conus gap A2 are arbitrarily determined so as to demonstrate suitable retention strength (for example, K1=6 degrees, A2=0.1 mm).

Thickness A1 is determined based on abutment surface data 103 and denture model data 109 to be values such that the height of inner crown 102 from margin line 104 to the inner crown upper surface 106 enables the demonstration of suitable retention strength. In addition, these may be arbitrarily determined by the user, or they may be determined by, for example, displaying abutment surface data 103, denture model data 109 and so forth on a PC screen and then referring (visually) to them. Furthermore, both thickness and gap are roughly zero at the margin line.

Transmission

In producing a conus in the manner of this example, all that is required is the surface data of the abutment 103 and a plurality of parameters (cement space S, conus angle K1, conus inner crown upper portion thickness A1, rise angle K2 and outer crown upper portion thickness A3), and these parameters and data are then transmitted.

Furthermore, although the margin line 104 may be determined from the data of the abutment 103, in the case of reflecting the operation of the user, it is preferable to add margin line data to this.

In addition, there are also cases in which a step is added in which this data is temporarily restored at the transmitting side, displayed on a monitor followed by adjustment of the data by operation of the screen by the user.

Denture model 109 can be restored by transmitting only the upper occlusal surface, machining data and margin line to the maximum surrounding projection as well as occlusal surface and height parameters. Since this data is small in size, it may be sent to the E-mail address of another person in the form of an attachment in the manner of handling as e-mail by a user after converting to a file, or may be sent in a size that can be dragged and dropped to a prescribed area of a computer of another person using a dialup format.

There are also cases in which a dialup connection is preferable in which the connection is terminated automatically as in the case of e-mail.

In the case of transmission, text data at the time of machining may be attached, or if there are instructions and so forth regarding the prosthesis, that data may also be attached.

Examples of applicable materials include titanium and ceramics. Titanium is known to be lightweight and have affinity for the body (Y. Miura, et al., General Chemical Theory, No. 21, pp. 85–96 (1978), and although that having as high a purity as possible is preferable, during its machining, since there are many cases in which a special drill is required for cutting and grinding, and since a proper machining environment must be provided, machining at a specialized machining site in this manner makes it possible to produce and supply prostheses both rapidly and appropriately.

In addition, it is more preferable to use titanium materials to produce comparatively large prostheses such as linked crowns, bridges, dentures, metal plates, clasps, palatal bars, lingual bars and so forth. This is similarly preferable in the case of using hard blocks such as ceramics or expensive materials.

Reception

A machining site at which data has been acquired by reception by, for example, e-mail, a so-called virtual shape is displayed on the production screen on a computer based on this data. Depending on the case, this may be resent to the user for confirmation.

Specific Data Production

Data 105, which indicates the shape of the lower surface of inner crown 102, is produced by calculation to add cement space S1 the data the abutment surface data above margin line 104. Data 106, which indicates the shape of the upper surface of inner crown 102, is produced by calculation from the data of margin line 104, conus angle K1 and inner crown upper portion thickness A1.

The portion of data 107 inside the margin line 104, which indicates the shape of the lower surface of outer crown 101, is produced by calculation from upper surface data 106 of inner crown 102 and conus gap (A2: mm). Data 108, which indicates the shape of the outer surface of outer crown 101, is produced by calculation to connect the maximum projection line and margin line in a plane, or from rise angle (K2: degrees). The upper surface of denture model data 19 is produced using measurement data.

In the case when the outer crown 101 and the denture model data 109 are separate from each other, as shown in FIG. 10, and in the case of, for example, dividing into a structure consisting of the outer crown 101 of a metal frame and a resin or porcelain material, etc. joined on top of it, the thickness (mm) of the outer crown 101 (indicated with A3 in FIG. 11) can be set automatically or manually and calculated therefrom. In the case of producing data for the resin or porcelain material on top of it, it is calculated from upper portion data 108 of the outer crown 101 (metal frame) and denture model data 109. If the upper surface 108 of the outer crown 101 has the outer crown 101 and denture model data 109 integrated into a single unit, upper portion data 108 of the outer crown 101 is omitted, and the thickness of the outer crown 101 coincides with the surface data of denture model data 109.

Machining

The material is selected and machining is carried out using an NC machine tool and so forth based on other data specified by the user.

Delivery

If a time is specified by the user, either delivery is requested to a third party delivery service or is hand-delivered by that time. Furthermore, if the machining device is in the movable state by an automobile or other means, machining and production may be carried out by going to a location near the user, or in the case machining devices are installed at various locations, data may be resent to that location followed by machining and hand-delivery to the user.

Figure 12:
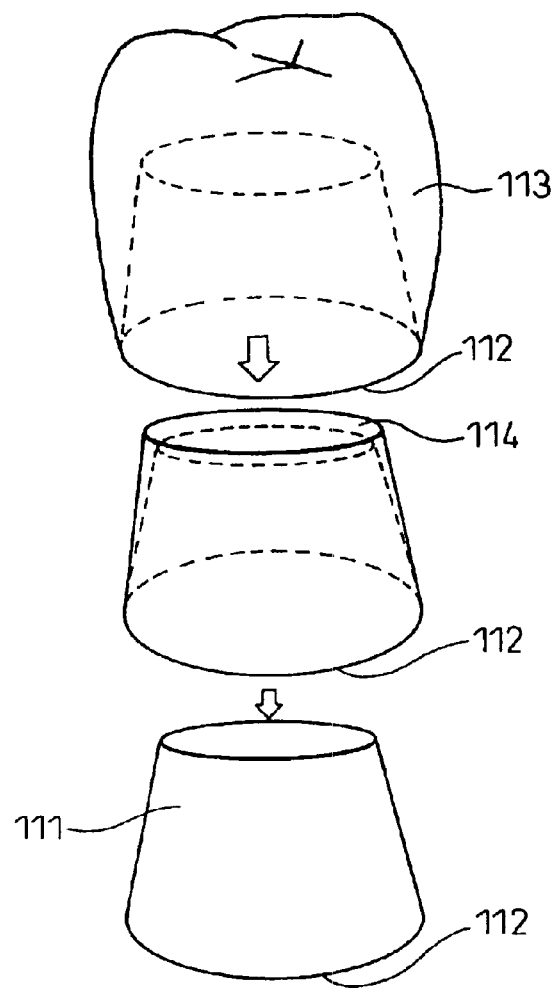
FIG. 12 is a cross-sectional view in the case of producing a metal coping type of prosthesis.
Figure 13:
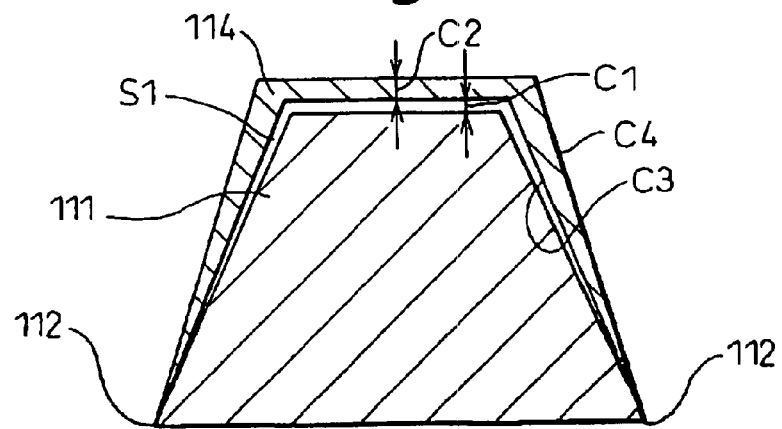
FIG. 13 is a cross-sectional view with the elements of FIG. 12 being combined.

FIGS. 12 and 13 are explanatory views for production of a metal coping type of prosthesis.

Metal coping refers to a metal structural body of a crown inner portion that is produced so as to be able to adequately demonstrate the material characteristics of porcelain materials or hard resin, and while giving consideration so that the strength of each restored portion can be guaranteed in a porcelain-baked cast crown or hard resin pre-coated crown. It may also be simply referred to as coping.

In the broad sense, coping is referred to as transfer coping that made of metal or resin for accurately reproducing the positional relationship on a model with a metal structural body (metal coping) of the inside of a crown pre-coated with a porcelain material or resin. It may also refer to paralleling coping that is made on an implant abutment and secures levelness with other abutments or natural teeth, or to telescope coping (secondary coping) that is equivalent to the outer crown of a telescope. In addition, it may also simply indicate coping.

Model Production

A model of the site of the abutment 111 is produced in the manner described above.

Measurement of Model Surface

Abutment data 111 is obtained by three-dimensionally measuring the surface status of abutment 111 as shown in the above embodiments. At this time, the margin line is made to be able to be discriminated by trimming the portion below the margin and so forth.

Setting of Parameters from Measurement Data

Margin line 112 is detected from the measurement data. This is preferably confirmed and corrected on a screen by the user. The thickness (mm) of cement space S1 (indicated with C1 in FIG. 13) and the thickness (mm) of coping 114 (indicated with C2 in FIG. 13) are determined. Reference numeral 113 indicates the denture model.

Transmission

The surface data of the abutment 111, thickness value C1 of cement space S1, coping thickness value C2 and other parameter data is transmitted, and the previous description should be referred to for the state of that transmission. Furthermore, although the margin line 112 may be determined from the data of abutment the 111, in the case of reflecting the operation of the user, margin line data is preferably added to this.

Production of Data Following Reception

Surface data C3 of the lower surface (inner surface) of coping 114 is obtained from the data of margin line 112 by adding the cement space to the surface data of abutment 111 above it by calculation. Surface data C4 of the upper surface of coping 114 is obtained by calculating from surface data C3 of the lower surface (inner surface) of coping 114 and the thickness value (C2) of coping 114. In the vicinity of margin line 112, C1 and C2 are changed intentionally so as to respectively coincide with the margin line. Surface data of the top and bottom of the coping can also be restored with only abutment data and a plurality of parameters.

Machining and Delivery

The inner surface of the outer crown is machined based on other data from the user and the above data of the top and bottom of the coping. Delivery is carried out in the manner described above.

As is described above, the present invention has the effect of enabling efficient transmission of dental measurement data and ensuring stable prostheses.

LIST OF REFERENCE NUMERALS

1 Measuring and machining terminal
2 Measuring and machining terminal
11 Measuring section
12 Machining section
13 Control section
14 Memory
15 Monitor
16 Server
17 Memory
18 Monitor
19 Telecommunications line
21 Display
22 Window
23 Icon group
24 Window
25 Window
26 File
27 File
28 Cursor
31 Display 32 Shared file
33 Icon group
34 Window
35 Icon
36 Display area
41 Measuring section
42 Machining section
43 Measuring stage
44 Probe
45 Drill
46 Support stage
47 Nozzle
48 Monitor
49 Panel switches
50 Drive section
51 Mouse
52 Modem
53 Modem
54 Connection mediation means
55 Connection mediation means
56 Communication line
57 Server
61 Drive unit
62 Base plate
63 Terminal support body
64 Detection unit
65a–65d Contacts
66 Support shaft
67 Electrical connection member
68 Drive signal output unit
69 Control means
70 Transmission unit
71 Transmission unit
72 Connection end
73 Motor
74 Sliding member
75 Other end
76 Potentiometer
77 Motor
78 Drill
79 Control means
80 Connector
81 Measurement device main unit
82 Parallel link driver
83 Cross probe
84 Measurement processing unit
85 Network
86 Machining processing unit
87 Machining device
88 Drive unit
89 Block to be machined
90 Recording medium
91 Connector
92 Transport
93 Network connection
94 Connector
95 Connector
96 Connector
97 Connector
98 Machining tool
101 Outer crown
102 Inner crown
103 Abutment data
104 Margin line
105 Inner crown inner surface shape
106 Inner crown upper surface shape
107 Outer crown inner surface shape
108 Outer crown upper surface shape
109 Denture model data
111 Abutment
112 Margin line
113 Denture model data
114 Coping

What is claimed is:

1. A dental measuring and machining system comprising:
a probe having contacts extending in the directions of a cross for contacting and measuring the surface of a model for producing a prosthesis;
a parallel link drive unit for driving said probe;
surface shape acquisition means for obtaining the surface shape of said model based on the contact by said probe; and
means for transmitting data acquired with said surface shape acquisition means; and
machining means that receives said transmitted data and machines a model for a prosthesis with a cutting tool or a grinding tool based on the received data.

2. The dental measuring and machining system according to claim 1 wherein a driver driving said cutting tool or the grinding tool has a parallel link structure.

3. The dental measuring and machining system according to claim 1, wherein said surface shape acquisition means is operable from the outside of said system.

4. The dental measuring and machining system according to claim 1, wherein said means for transmitting data comprises at least one of an internet, an E-mail, and a delivery of an information storing medium.

* * * * *